United States Patent [19]

Knott et al.

[11] Patent Number: 4,486,328
[45] Date of Patent: Dec. 4, 1984

[54] BETAINE-SOAP SHAMPOO COMPOSITION

[75] Inventors: Christine A. Knott, Manchester; Joyce Ryan, Bolton, both of England

[73] Assignee: Colgate-Palmolive Company, New York, N.Y.

[21] Appl. No.: 491,010

[22] Filed: May 3, 1983

[51] Int. Cl.³ .......................... C11D 9/30; C11D 1/84
[52] U.S. Cl. .................................. 252/117; 252/546; 252/547; 252/DIG. 13
[58] Field of Search .............. 252/117, 546, 547, 548, 252/DIG. 13; 424/70

[56] References Cited

U.S. PATENT DOCUMENTS

| | | | |
|---|---|---|---|
| 3,590,122 | 6/1971 | Roberts et al. | 424/70 |
| 3,711,414 | 1/1973 | Hewitt | 252/118 |
| 3,755,559 | 8/1973 | Hewitt | 424/70 |
| 3,957,970 | 5/1976 | Korkis | 424/70 |
| 4,064,076 | 12/1977 | Klisch et al. | 252/542 |
| 4,312,771 | 1/1982 | Matsuda | 252/107 |
| 4,329,334 | 5/1982 | Su et al. | 424/70 |

FOREIGN PATENT DOCUMENTS

| | | |
|---|---|---|
| 40125 | 12/1975 | Japan . |
| 31708 | 3/1976 | Japan . |
| 26805 | 3/1978 | Japan . |

Primary Examiner—Prince E. Willis
Attorney, Agent, or Firm—Richard N. Miller; Murray M. Grill; Herbert S. Sylvester

[57] ABSTRACT

A mild, clear, liquid shampoo having good cleaning and foaming properties in hard and soft water in the absence of water-soluble, anionic, sulphonated and sulphated detergents is disclosed which consists essentially of from 6% to 24% by weight of a mixture of a water-soluble zwitterionic detergent corresponding to the formula

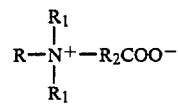

wherein R is $C_8$–$C_{18}$ or $C_8$–$C_{18}$ alkanamido $C_2$–$C_3$ alkyl, $R_1$ is $C_1$–$C_3$ alkyl and $R_2$ is $C_1$–$C_4$ alkylene or $C_1$–$C_4$ hydroxyalkylene and a water-soluble salt of $C_{10}$–$C_{18}$ carboxylic acid selected from the group consisting of sodium, potassium, ammonium and $C_2$–$C_3$ alkanolammonium salts, the mole ratio of said zwitterionic detergent to carboxylic acid salt being from 1.2:1 to 2.3:1, 1% to 8% by weight of $C_8$–$C_{18}$ carboxylic $C_2$–$C_3$ alkanolamide; and an aqueous medium, said shampoo having a pH of from 7.5 to 9. Preferred shampoos contain triethanolamine myristate, $C_8$–$C_{18}$ alkanamido $C_2$–$C_3$ alkyl dimethyl betaine and coconut fatty acid diethanolamide as essential ingredients and include free triethanolamine, a sequestering agent and/or a solubilizing material as optional components.

8 Claims, No Drawings

BETAINE-SOAP SHAMPOO COMPOSITION

FIELD OF THE INVENTION

This invention relates to a clear, liquid shampoo composition based upon a mixture of a water-soluble soap and a zwitterionic detergent which exhibits cleansing and foaming properties in hard and soft water that are comparable to shampoos based upon anionic sulfonated and sulfated detergents. As the inventive compositions are free of said anionic sufactants which tend to be skin irritants, the inventive shampoo is milder to the skin.

BACKGROUND OF THE INVENTION AND PRIOR ART

Because of the known deleterious effects on the skin of the anionic sulfate and sulfonate detergents commonly used in shampoos, research efforts continue to be directed towards the formulation of milder shampoos which are free of such sulfated and sulfonated surfactants but which exhibit the cleansing and foaming characteristics of shampoos containing said commonly used sulfated and sulfonated surfactants. Furthermore, with the emphasis on use of naturally derived ingredients, shampoos containing water-soluble soap as a surfactant in place of said sulfated and sulfonated detergents have present-day marketing appeal, too.

Prior to the commercialization of the anionic sulfated and sulfonated detergents, e.g., sodium or triethanolamine lauryl sulfate, ammonium $C_8$–$C_{18}$ alkyl monoglyceride sulfate, sodium $C_9$–$C_{15}$ alkylbenzene sulfonate, etc., liquid shampoo compositions employed potassium soaps as the primary surfactant. For example, liquid shampoos containing potassium soaps are shown in Chapter 19 of "Cosmetics, Science and Technology" edited by Sagarin and in U.S. Pat. No. 4,312,771 in combination with a $C_8$–$C_{18}$ fatty acid monoethanolamide. While such shampoos were very satisfactory in soft water, they were less than completely satisfactory in hard water due to the formation of water-insoluble calcium and magnesium soap curds.

With the commercialization of synthetic detergents such as the alkyl sulfate salts, alkylbenzene sulfonate salts, zwitterionic detergents, etc., mixtures of soap and a synthetic organic detergent often were employed in shampoos. For example, U.S. Pat. No. 3,660,470 discloses shampoo compositions containing a mixture of soap and a zwitterionic detergent in which the ratio of soap to zwitterionic detergent is from 3:1 to 100:1. Similarly, U.S. Pat. No. 3,957,970 discloses shampoos containing 50-60% by weight of soap, fatty acid alkanolamide, and 40-60% by weight of a synthetic organic detergent such as sodium lauryl sulfate or a mixture of triethanolamine lauryl sulfate and $C_8$–$C_{18}$ alkanamido-propyl dimethyl betaine. U.S. Pat. No. 3,988,438 discloses a shampoo containing a mixture of a major proportion of soap and up to 5% by weight of the triethanolamine salt of alginic acid. On the other hand, Norda Briefs disclose soap-free shampoos containing a mixture of alkyl sulfate, zwitterionic betaine and fatty acid diethanolamide as does U.S. Pat. No. 3,950,417 which discloses shampoos containing zwitterionic betaine, alkyl sulfate and polyoxyethylene sorbitan monolaurate. However, with the exception of U.S. Pat. Nos. 3,660,470 and 3,988,488, all of the foregoing shampoo compositions contain a skin-irritating anionic sulfated or sulfonated surfactant as an essential ingredient.

Although the patents discussed above appear to suggest either mixtures of soap and anionic sulfonated or sulfated detergents or, alternatively, non-soap, anionic sulfated or sulfonated detergents for use in shampoos, some shampoos comprising mixtures of soap and zwitterionic detergents are disclosed. One such patent is U.S. Pat. No. 3,660,470 and another patent is U.S. Pat. No. 3,767,584. In these patents, soap is employed as the principal surfactant, an approach which is consistent with the teachings in U.S. Pat. No. 3,536,628 wherein a minor proportion of a zwitterionic detergent is included in a soap bar.

The inventive shampoo differs from the prior art compositions in that it is based upon a mixture of soap and zwitterionic detergent wherein the zwitterionic detergent is present in a major proportion, but in a prescribed molar ratio. Further, no anionic sulfate or sulfonated detergent is included; but, surprisingly, the resultant shampoo has cleaning and foaming properties which are equivalent to non-soap shampoos containing a mixture of alkyl sulfate and fatty alkanolamide. An additional characteristic of the inventive shampoos is their mildness.

SUMMARY OF THE INVENTION

As indicated above, the present invention resides in the discovery that shampoos containing water-soluble soap which have effective cleansing and foaming properties in both hard and soft water can be achieved in the absence of anionic sulfated and sulfonated detergents if a major proportion of a zwitterionic detergent and a minor proportion of soap are present with a carboxylic acid alkanolamide. Also, the resultant shampoos are mild to the skin and are clear, stable liquids because of the use of controlled proportions of zwitterionic detergent and soap. Furthermore, the controlled proportions of the three essential ingredients provide a desirable creamy foam having good stability in the presence of soil.

Broadly, the present invention relates to a mild, clear, liquid shampoo composition which is free of water-soluble, anionic, sulfonated and sulfated detergents and consists essentially of from 6% to 24% by weight of a mixture of a water-soluble zwitterionic detergent corresponding to the formula

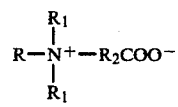

wherein R is $C_8$–$C_{18}$ alkyl or $C_8$–$C_{18}$ alkanamido $C_2$–$C_3$ alkyl, $R_1$ is $C_1$–$C_3$ alkyl and $R_2$ is $C_1$–$C_4$ hydroxyalkylene and a water-soluble salt of $C_{10}$–$C_{18}$ carboxylic acid selected from the group consisting of sodium, potassium, ammonium and $C_2$–$C_3$ alkanolammonium salts, the mole ratio of said zwitterionic detergent to carboxylic acid salt being from 1.2:1 to 2.3:1; 1% to 8% by weight of $C_8$–$C_{18}$ carboxylic acid $C_2$–$C_3$ alkanolamide; and aqueous medium, said shampoo having a pH of from 7.5 to 9.

In a preferred aspect, a mixture of mono-, di- or tri-ethanolammonium $C_{12}$–$C_{16}$ carboxylate and a $C_8$–$C_{18}$ alkanamido $C_2$–$C_3$ alkyl dimethyl betaine is employed together with 0.2% to 7% by weight of free mono-, di- or tri-ethanolmine base to yield a shampoo with optimal performance and physical characteristics. These desirable characteristics appear to be due to the controlled proportions of the particular essential ingredients incorporated therein.

DETAILED DESCRIPTION OF THE INVENTION

The principal surfactant ingredient in the inventive mild, liquid compositions is a zwitterionic detergent corresponding to the formula

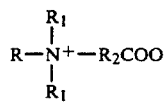

wherein R is a $C_8-C_{18}$ alkyl or $C_8-C_{18}$ alkanamido $C_2-C_3$ alkyl, $R_1$ is $C_1-C_3$ alkyl and $R_2$ is a $C_1-C_4$ alkylene or $C_1-C_4$ hydroxy alkylene. This type of detergent often is called a betaine. These zwitterionic detergents can be described broadly as derivatives of an aliphatic quaternary ammonium compound containing a $C_8-C_{18}$ aliphatic radical which may be straight chained or branch chained and an anionic group. Preferred betaine detergents are lauryl dimethylammonioacetate, myristlydimethylammonioacetate and $C_8-C_{18}$ alkanamidopropyldimethylammonio acetate, with the latter detergent being most preferred.

In the inventive compositions, the zwitterionic detergent acts as the primary cleaning and foaming agent. Also, it functions as a curd dispersant for any calcium and magnesium soaps which form in hard water. Further, in combination with the supplementary soap ingredient, it produces a creamy, lubricious foam in both hard and soft water.

The supplementary surfactant ingredient in the inventive, mild liquid compositions is a water-soluble soap. Suitable water-soluble soaps which can be used in the shampoo compositions of this invention are the water-soluble salts of carboxylic acids containing 10 to 18 carbon atoms, preferably 12-16 carbon atoms, in the acyl group. The salt-forming cation may be sodium, potassium, ammonium or $C_2-C_3$ alkanolammonium, with the ammonium and di- or tri-ethanolammonium cations being preferred. The suitable $C_2-C_3$ alkanolammonium cations include mono-, di- and tri-ethanolammonium; mono-, di- and tri-isopropanol ammonium; 1-hydroxy-2 methyl-2 propyl ammonium (AMP); 1-3 dihydroxy-2 methyl-2 propyl ammonium (AMPD); and N-methyl-N-(1-hydroxy-2 methyl-2 propyl) ammonium (DMAMP). Such soaps can be made by direct saponification of natural oils, e.g., coconut oil or palm kernel oil, or they can be made by neutralization of either fatty acids derived from natural oils or from alkanoic acids derived synthetically. Soaps derived from natural oils, either directly or indirectly, are essentially straight-chained; whereas, soap obtained from synthetic sources can be either straight or branched chained. Preferred soaps are salts of fatty acids derived from natural oils, with salts of myristic acid being particularly preferred.

In the shampoo compositions of this invention the proportion of surfactant, i.e., the sum of the concentration of water-soluble zwitterionic detergent and the concentration of water-soluble soap, generally will be from 6% to 24%, preferably 8% to 18%, by weight. Further, the mole ratio of zwitterionic detergent to soap generally will be in the range of 1.2:1 to 2.3:1, preferably about 1.4:1 to 1.7:1. The ratio of zwitterionic detergent to soap is important because compositions wherein soap is present in major proportion—the weight ratio is too low—exhibit physical instability as well as foaming deficiencies. Similarly, where the zwitterionic detergent to soap ratio is too high, the foaming properties of the shampoo are adversely affected.

The final essential ingredient in the mild liquid detergent composition is a $C_8-C_{18}$ carboxylic acid $C_2-C_3$ alkanolamide. This component is widely recognized as a foam builder and satisfactory carboxylic acid alkanolamides are lauric monoethanolamide, myristic monoethanolamide, lauric diethanolamide, myristic diethanolamide, lauric isopropanol amide and coconut fatty acid ($C_8-C_{18}$) monoethanolamide. Preferred carboxylic acid alkanolamides are coconut fatty acid ($C_8-C_{18}$) diethanolamide and lauricmyristic acid ($C_{12}-C_{14}$) diethanolamide.

As indicated above, the carboxylic acid alkanolamide improves the foam quality, particularly in the presence of sebum soil. Usually, the proportion of the carboxylic acid alkanolamide will be from 1% to 8%, preferably 2% to 5%, by weight of the final shampoo composition.

Usually, the balance of the liquid composition will be an aqueous medium comprising water and, optionally, up to 10%, preferably 1% to 8%, by weight of a viscosity modifier selected from the group of $C_2-C_3$ monohydric alcohols, e.g., ethanol and isopropanol, and suitable polyhydric alcohols, e.g., glycerol and propylene glycol with propylene glycol being preferred. Typically, the modifier is selected to provide clarity and/or a low temperature cloud point and to control viscosity. Since the alcohol and urea solubilizers do not exhibit the same effects, the liquid compositions may contain a mixture of alcohol and urea, particularly where the desired low-temperature cloud temperature or viscosity cannot be achieved in the absence of urea.

An important characteristic of the claimed compositions is the absence of the anionic sulfated and sulfonated detergents which are the predominant detergent components used in present-day shampoos. Since such detergents are known to be skin irritants, the inventive shampoos are more mild to the skin. In fact, the mildness of the inventive shampoos is enhanced further by the use of the soap in combination with the water-soluble zwitterionic detergent ingredient since shampoos containing soap as the sole detergent component also have been found to be skin irritants. Surprisingly, however, the inventive shampoos are equivalent in foaming and detergency performance to the shampoos based upon anionic sulfonate and sulfate detergents in water of 0 to 300 ppm of hardness expressed as calcium carbonate. This latter observation is somewhat surprising because it is suggested in the prior art that soap tends to depress the foam volume of other organic detergents.

The described mild liquid compositions are essentially unbuilt liquids, i.e., do not contain amounts of organic or inorganic salt in detergent building proportions and, therefore, are suitable for use as shampoos and foam or liquid shower bath products. Thus, these inventive compositions can contain any of the usual adjuvants found in those compositions provided that they do not interfere with the mildness or performance properties of the inventive liquids. Such additional ingredients include minor proportions of perfumes and colors for aesthetic purposes; opacifiers such as ethylene glycol distearate or polystyrene; thickening agents such as natural gums or hydroxypropyl methyl cellulose; sequestering agents such as sodium citrate or tetrasodium ethylenediamine tetraacetate, with the latter being preferred; preservatives such as formaldehyde or Dowicil ®200 or monoethyloldimethyl hydantoin; fluorescent agents or optical whiteners; magnesium sulphate; inert salts such as sodium sulphate; and perfume stabilizers such as ethoxylated (40 EO) hydrogenated castor oil. The total concentration of added ingredients usually will be less than 5%, preferably less than 3%, by weight of the total composition.

Generally, the pH of the inventive shampoo compositions will be in the range of about 7.5 to 9, preferably 8 to 8.5. Optionally, an excess of the basic material used to provide the cation of the water-soluble soap, e.g., sodium, potassium or ammonium hydroxide or mono-, di- and triethanolamine or AMP, AMPD and DMAMP, is employed. While the concentration of excess basic material will vary with the concentration of the carboxylic acid salt and the identity of said material, generally a concentration of from 0.2% to 7%, preferably 0.5% to 4%, by weight will be sufficient to yield a pH within the desired range.

Similarly, the viscosity of the liquid shampoo will be variable over the range of about 500 centipoises (cps.) to 4,000 cps., and preferably from 1,000 to 2,500 cps. Viscosity is measured using a Brookfield Viscometer, Model RVT, with a #3 spindle rotating at 20 rpm. The most preferred viscosity range is 1,000 cps. to 2,000 cps. based upon current consumer preference. However, it will be recognized by one skilled in the art that liquids of either lower or higher viscosity can be achieved by including either an appropriate amount of a known thickening agent or, alternatively, an appropriate amount of alkanol solubilizer in the inventive compositions.

In manufactruring the shampoo compositions, usually the fatty acid soap is dissolved in water with agitation and heating, if necessary, to obtain an homogeneous solution. The soap solution is then cooled to 40° C. or below. Thereafter the formula amounts of aqueous zwitterionic betaine (30-45% by weight of betaine) and carboxylic acid alkanolamide are added with agitation and mixing is continued until homogeneity is achieved. If a viscosity modifying agent is needed to attain homogeneity, it may be added either before or after the addition of the betaine and alkanolamide. Then, any optional ingredients, e.g., sequestering agent, preservative, color, perfume, perfume solubilizer, etc., usually are added. If necessary, the pH of the shampoo is adjusted by the addition of an appropriate amount of acid or base, whichever is indicated.

If desired, the water-soluble carboxylic salt may be prepared in situ by addition of the formula proportion of carboxylic acid in an aqueous solution containing the formula proportion of the neutralizing agent for said carboxylic acid. Both parts being maintained at 75° C. to 80° C. The in situ neutralization process appears to facilitate control of product quality and, therefore, is preferred.

One of the methods used to determine the detergency and foaming properties of the shampoo is a modified version of a method unofficially adopted by the French Association for Informative Labelling (AFEI). The object of the method is to measure the "Potential shampooing power" for labelling purposes. In such method, a small panel of volunteers with medium length hair and average soiling is employed. Using a half-head procedure, the amount of test shampoo is adjusted until the quantity of foam produced is judged to be equal to the foam produced by a fixed amount of a standard shampoo. A simple calculation will then indicate the number of shampoos which can be obtained from 100 ml. of the shampoo product. In this test, the desired amount of foam is the amount produced using six grams of a standard shampoo containing 12% by weight of sodium lauryl diethenoxy ether sulfate and 3% by weight of coconut fatty acid diethanolamide in a first wash and four grams of said shampoo in the second wash. The foam in the first wash is generated by the operator by massaging the shampoo into wet hair with the finger tips for one and one-half minutes. In the second wash, the foam is worked up for one minute. In the actual test, the standard shampoo is applied to one half of the head of panelist one—three grams in the first wash and two grams in the second wash—and identical amounts of the test shampoo are applied to the other half of the head. Based upon the results of the first panelist, the amount of test shampoo is adjusted upward or downward in 0.1 gram increments using as many panelists as necessary until equal quantities of foam are noted by three consecutive panelists. The side of the head to which the standard shampoo is applied is alternated to compensate for the right- or left-handedness of the operator. Both quantity and texture of the foam are scored after each wash, with the hair being rinsed completely after each wash.

Another test employed to measure the foaming characteristics of the shampoo compositions is the Tress Foaming Test. This method takes into consideration the fibre to fibre interactions which take place in the hair shampoo process. In this test foaming properties are evaluated by a given number of panelists on $20 \times 4$ g $\times$ 10-inch long tresses of untreated dark brown Italian hair. All the tresses are pre-washed with a secondary alkane sulphonate detergent, rinsed under running water for three minutes and allowed to dry naturally prior to use. The first panelist is assigned a numbered pre-washed tress which is wetted in a standard manner. The panelist holds the wetted, coiled tress in the left hand, and then 1.5 ml. of either the standard composition or the test composition is applied to the tress. The foam is worked up with the fingertips of the right hand for thirty seconds using a circular motion. The panelist rinses the tress under running water for thirty seconds. The order in which the panelist evaluates the two compositions is randomly assigned, and the identity of the compositions is also unknown to the panelist.

Each panelist rates the rate of foam build-up, amount of foam, foam texture, foam stability and ease of rinsing using a scale of 1 to 10. (A rating of 1 or 2 is very poor, 5 or 6 is moderate, and 9 or 10 is very good for each variable tested.) Each test is repeated by subsequent panelists until each composition is rated ten times. Thereafter, the tresses are washed again with secondary alkane sulphonate detergent, rinsed under running water for three minutes and allowed to dry naturally. Then each composition is crossed over and rated again by the same panelist. Scores are analysed statistically by means of a paired T test to find significant differences.

Specific inventive liquid compositions are illustrated by the following examples. All quantities indicated in the examples or elsewhere in the specification are by weight unless otherwise stated.

EXAMPLE 1

A preferred liquid shampoo composition in prepared from the following listed components.

|  | % by weight |
|---|---|
| Myristic acid | 3.0 |
| Triethanolamine | 4.0 |
| Cocoamidopropyldimethyl betaine* | 7.0 |
| Coconut fatty acid diethanolamide | 3.0 |
| Tetrasodium ethylenediamine tetraacetate (EDTA, Na₄) | 0.15 |
| Formaldehyde | 0.04 |
| Hydrogenated castor oil ethoxylate (40 EO)** | 0.4 |
| Perfume | 0.4 |
| Water | q.s. |
|  | 100.00 |

*Coco is $C_8$-$C_{18}$ alkyl
**Perfume solubilizer

The foregoing shampoo has a pH in the range of 8–8.5 and is a clear liquid at room temperature (25° C.) It has a viscosity of 1,400 centipoises as measured with a Brookfield RVT Viscometer using a No. 3 spindle rotating at 20 rpm.

The preferred shampoo composition is prepared by mixing four parts by weight of triethanolamine with 65.25 parts by weight of water maintained at 75° C.–80° C. and then adding three parts by weight of molten myristic acid at 80° C. with agitation to form an aqueous solution containing about five parts by weight of triethanolamine myristate and about two parts by weight of free triethanolamine. This mixture is maintained at 80° C. for fifteen minutes. A premix of coconut fatty acid diethanolamide, cocoamidopropyldimethyl betaine, EDTA and formaldehyde is prepared by mixing said diethanolamide with a 30% aqueous mixture of said betaine and thereafter adding a 30% aqueous solution of EDTA and a 40% aqueous solution of formaldehyde to said mixture with agitation. The foregoing premix is mixed with the solution of triethanolamine myristate and free triethanolamine at a temperature of about 40° C. Finally, the hydrogenated castor oil ethoxylate and the perfume are premixed and added with agitation to yield the desired shampoo.

When the preferred shampoo of example I is tested against a standard shampoo containing 12% by weight of sodium lauryl diethenoxy ether sulphate and 3% by weight of coconut fatty acid diethanolamide—a typical, prior-art anionic shampoo—in the foregoing unofficial method of AFEI, the foaming and cleansing properties of the preferred shampoo are observed to be equivalent to the prior art, anionic detergent shampoo in both soft and hard (300 ppm.) water.

EXAMPLES 2–4

The composition of Example 1 is repeated with the exception that the concentration of cocoamidopropyldimethyl betaine is changed from 7% to 5.5% (Example 2), 6% (Example 3) and 10% (Example 4) by weight respectively and the concentration of water is adjusted accordingly. All shampoos are clear liquids at room temperature (25° C.).

When the foaming properties of the compositions of Examples 1–4 are evaluated against the standard shampoo described in Example 1 using the Tress Foaming Test by twenty panellists in water of 30 ppm hardness, the results shown in Table I are obtained.

TABLE I

|  | Valuation Rating | | | | | | | |
|---|---|---|---|---|---|---|---|---|
|  | Std. | Ex. 2 | Std. | Ex. 3 | Std. | Ex. 1 | Std. | Ex. 4 |
| Rate of foam | 7.30 | 6.85 | 6.8 | 6.65 | 6.55 | 6.25 | 6.90 | 6.90 |
| build-up |  |  |  |  |  |  |  |  |
| Amount of foam | 7.40 | 6.60 | 7.30 | 6.10[b] | 6.55 | 5.95 | 7.15 | 6.25[a] |
| Foam texture | 5.85 | 7.65[d] | 5.60 | 7.50[c] | 5.65 | 8.05[c] | 6.05 | 7.80[c] |
| Foam stability | 6.40 | 6.90 | 5.95 | 7.10[d] | 5.80 | 7.35[c] | 6.35 | 7.20[d] |
| Ease of rinsing | 6.80 | 7.35 | 6.50 | 6.80 | 6.45 | 6.70 | 6.70 | 6.75 |

[a]Difference significant at 95% confidence level according to statistical analysis based upon paired T test.
[b]Difference significant at 98% confidence level according to statistical analysis based upon paired T test.
[c]Difference significant at 99.9% confidence level according to statistical analysis based upon paired T test.
[d]Difference significant at 99% confidence level according to statistical analysis based upon paired T test.

The results in Table I show that the inventive compositions exhibit substantially the same foaming properties as the standard shampoo. Further, the results show that the preferred composition of Example I exhibits significant superiority over the standard shampoo in foam texture and foam stability.

EXAMPLE 5

The composition of Example 1 is repeated with the exception that the concentration of triethanolamine is reduced from 4% to 2% by weight and the amount of water is increased by 2% by weight. The resulting shampoo is a clear liquid at room temperature (25° C.) and exhibits a viscosity of 3,000 cps. as measured using a Brookfield RVT Viscometer with a #3 spindle rotating at 20 rpm. Further, samples aged for one month at 43° C., 25° C. and 4° C. respectively are clear.

EXAMPLES 6 AND 7

When the composition of Example 5 is repeated using 6% and 10% by weight of cocoamidopropyldimethyl betaine instead of 7%, compositions having pH's of 8.15 and 8.10 are achieved. Such compositions are clear liquids after aging for one month at 43° C., 25° C. and 4° C.

When the proportion of cocoamidopropyldimethyl betaine in the composition of Example 5 is reduced to 3% by weight or 5% by weight, stability is adversely affected. For example, at 3% by weight the shampoo is not completely clear at 25° C. and separates after one month of aging at 43° C. On the other hand, at 5% by weight, a white precipitate is noted after aging at 4° C. for three months. However, when 2% by weight of free triethanolamine is present in the compositions containing 3% and 5% by weight of betaine, the resultant compositions are clear after aging for three months at 43° C., 25° C. and 4° C.

EXAMPLE 8

Another satisfactory liquid shampoo composition having the following formula is prepared according to the process of Example 1.

|  | % by weight |
|---|---|
| Myristic acid | 3.0 |
| 1-hydroxy-2 methyl-2propyl amine (AMP) | 1.13 |
| Cocoamidopropyldimethyl betaine | 7.0 |
| Coconut fatty acid diethanolamide | 3.0 |
| Propylene glycol | 0.4 |
| EDTA, Na₄ | 0.15 |

-continued

|  | % by weight |
| --- | --- |
| Formaldehyde | 0.04 |
| Hydrogenated castor oil ethoxylate (40 EO) | 0.40 |
| Perfume | 0.40 |
| Water | q.s. |
|  | 100.00 |

The resultant shampoo has a pH of 8.4 and contains about 4.1% by weight of 1-hydroxy-2-methyl-2propyl ammonium myristate and no free amine base. It is a clear liquid at room temperature and its viscosity is about 1,150 cps as measured with a Brookfield RVT Viscometer using a #3 spindle rotating at 20 rpm. Compositions aged for one month at 43° C., 25° C. and 4° C. are clear liquids.

When the shampoo of Example 1 is compared with the standard anionic shampoo composition containing 12% by weight of sodium lauryl diethenoxyether sulfate and 3% by weight of coconut diethanolamide in the beauty salon using a panel of fifty persons, a trained evaluator found the two shampoos to be essentially equivalent in performance in hard water (300 ppm.). Similar equivalence is noted in salon tests with fifty panelists when the shampoo of Example 1 is compared with a commercial shampoo composition containing a mixture of anionic detergent, amphoteric detergent and a cationic polymer.

Substitution of lauryl dimethyl betaine for cocoamidopropyldimethyl betaine in the shampoo of Example 8 yields a shampoo with substantially equivalent performance characteristics.

EXAMPLE 9

Another satisfactory shampoo has the following composition:

|  | % by weight |
| --- | --- |
| Potassium myristate | 5.0 |
| Coconut diethanolamide | 3.0 |
| Cocoamidopropyldimethyl betaine | 7.0 |
| EDTA, Na4 | 0.15 |
| Formaldehyde | 0.04 |
| Hydrogenated castor oil ethoxylate (40 EO) | 0.40 |
| Perfume | 0.40 |
| Water | q.s. |
|  | 100.00 |

The foregoing shampoo is comparable to the shampoo of Example 1 in salon tests.

EXAMPLES 10 AND 11

Other suitable shampoo compositions follow:

|  | 10 | 11 |
| --- | --- | --- |
| Triethanolamine myristate | 2.5 | 10 |
| Propylene glycol | 0.0 | 3 |
| Coconut diethanolamide | 1.5 | 6 |
| Cocoamidopropyldimethyl betaine | 3.5 | 14 |
| EDTA, Na4 | 0.15 | 0.15 |
| Formaldehyde | 0.04 | 0.04 |
| Perfume | 0.40 | 0.40 |
| Hydrogenated castor oil ethoxylate (40 EO) | 0.40 | 0.40 |
| Water | q.s. | q.s. |
|  | 100.00 | 100.00 |

The importance of the zwitterionic detergent ingredient in the inventive shampoo compositions is illustrated by the fact that substitution of chemically similar detergents, e.g., sodium N-lauroyl sarcosinate or the triethanolamine salt of a condensate of an animal hydrolysate and $C_8$-$C_{18}$ fatty acid results in shampoo compositions having foaming deficiencies in hard and soft water. On the other hand, substitution of a $C_8$-$C_{10}$ alkyl glucoside—a detergent based upon a derivative of glucose—for up to about 50% by weight of the betaine in the composition of Example 1 yields a clear shampoo with good performance in hard and soft water.

The invention has been described with respect to various examples and illustrations thereof but is not to be limited to these because it is clear that one of skill in the art, with the present description before him, will be able to utilize substitutes and equivalents without departing from the invention.

What is claimed is:

1. A mild, clear, liquid shampoo composition which is free of water-soluble, anionic, sulphonated and sulphated detergents and consists essentially of from 6% to 24% by weight of a mixture of a water-soluble zwitterionic detergent corresponding to the formula

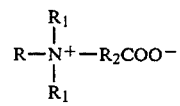

wherein R is $C_8$-$C_{18}$ alkyl or $C_8$-$C_{18}$ alkanamido $C_2$-$C_3$ alkyl, $R_1$ is $C_1$-$C_3$ alkyl and $R_2$ is $C_1$-$C_4$ alkylene or $C_1$-$C_4$ hydroxyalkylene and a water-soluble salt of $C_{10}$-$C_{18}$ carboxylic acid selected from the group consisting of sodium, potassium, ammonium and $C_2$-$C_3$ alkanolammonium salts, the mole ratio of said zwitterionic detergent to carboxylate being from 1.2:1 to 2.3:1; 1% to 8% by weight of $C_8$-$C_{18}$ carboxylic acid $C_2$-$C_3$ alkanolamide; and an aqueous medium; said shampoo having a pH of from 7.5 to 9.

2. A shampoo composition according to claim 1 wherein said carboxylic acid salt is a mono-, di- or triethanolammonium salt of a $C_{12}$-$C_{16}$ fatty acid.

3. A shampoo composition according to claim 1 wherein R is a $C_8$-$C_{18}$ alkanamido $C_2$-$C_3$ alkyl and $R_1$ is methyl in the zwitterionic detergent formula.

4. A shampoo composition according to claim 1 which includes, in addition, from 0.2% to 7% by weight of the basic material used to provide the cation of the carboxylic acid salt.

5. A shampoo composition according to claim 2 wherein R is a $C_8$-$C_{18}$ alkanamido $C_2$-$C_3$ alkyl and $R_1$ is methyl in said zwitterionic detergent formula, said concentration of the mixture of zwitterionic detergent and carboxylic acid salt is from 8% to 18% by weight, said mole ratio of zwitterionic detergent to carboxylic acid salt is from 1.4:1 to 1.7:1 and said carboxylic acid alkanolamide is present in an amount of 2% to 5% by weight.

6. A shampoo composition according to claim 5 wherein said carboxylic acid alkanolamide is $C_8$-$C_{18}$ fatty acid diethanolamide or lauric-myristic acid diethanolamide.

7. A shampoo according to claim 6 wherein said zwitterionic detergent is $C_8$-$C_{18}$ alkanamidopropyldimethyl betaine, said carboxylic acid alkanolamide is $C_8$-$C_{18}$ fatty acid diethanolamide and said carboxylic acid salt is triethanolamine myristate.

8. A shampoo according to claim 7 which includes, in addition, 0.5% to 4.0% by weight of free triethanolamine.

* * * * *